(12) United States Patent
Grimes et al.

(10) Patent No.: US 6,359,114 B1
(45) Date of Patent: *Mar. 19, 2002

(54) SYSTEM FOR METHOD FOR THE MODIFICATION AND PURIFICATION OF PROTEINS

(75) Inventors: Stephen Grimes; Stephen L. Karr, Jr., both of Davis, CA (US)

(73) Assignee: Aphton Corp., Woodland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/484,740

(22) Filed: Jun. 7, 1995

(51) Int. Cl.[7] .............................. C07K 1/14; C07K 1/34
(52) U.S. Cl. ......................... 530/344; 530/412; 530/414
(58) Field of Search ................................ 530/412, 414, 530/344

(56) References Cited

U.S. PATENT DOCUMENTS

| 4,042,682 A | | 8/1977 | Spector ........................ 424/95 |
| 4,420,425 A | * | 12/1983 | Lawhon ..................... 260/123.5 |
| 4,443,540 A | * | 4/1984 | Chervan et al. ................ 435/69 |
| 4,495,190 A | | 1/1985 | Hagberg et al. .............. 514/262 |
| 4,605,500 A | * | 8/1986 | Takemura et al. ......... 210/321.1 |
| 4,608,336 A | | 8/1986 | Benovic et al. ................ 435/7 |
| 4,609,662 A | | 9/1986 | Krenitsky ................... 514/262 |
| 4,621,140 A | | 11/1986 | Verheyden et al. .......... 544/276 |
| 4,762,913 A | | 8/1988 | Stevens ....................... 530/345 |
| 4,777,244 A | * | 10/1988 | Bonhard et al. ............. 530/385 |
| 4,803,170 A | | 2/1989 | Stanton et al. ............... 436/518 |
| 5,006,334 A | | 4/1991 | Stevens ........................ 424/88 |
| 5,023,077 A | * | 6/1991 | Gaves et al. .................. 424/88 |
| 5,106,734 A | | 4/1992 | Nielsen ........................ 435/84 |
| 5,188,733 A | | 2/1993 | Wang et al. ............ 210/321.84 |
| 5,316,728 A | | 5/1994 | Hayashi et al. ................ 422/70 |
| 5,683,916 A | * | 11/1997 | Goffe et al. ................. 436/535 |

FOREIGN PATENT DOCUMENTS

| EP | 0476875 | 3/1992 |
| WO | 9204970 | 4/1992 |
| WO | 9640733 | 6/1995 |

OTHER PUBLICATIONS

WPIDS on STN. No. 95–232095. Chen et al., CN1087946, Jun. 15, 1994 (Abstract only).*
E. Drioli et al "(catalytic membrane reactors)" *Chemistry & Industry* No. 1, 1996, pp. 19–22.
Brochure from AMICON re "Ultrafiltrations Systems"Publication 750 Technical Service 1987.
AMICON Brochure re Spiral–Wound/Hollow Fiber System pp. 54, 55, 8, 9, 24 and 25, 16 and 17 (copies).

* cited by examiner

*Primary Examiner*—Christopher S. F. Low
*Assistant Examiner*—Anish Gupta
(74) *Attorney, Agent, or Firm*—White & Case LLP

(57) ABSTRACT

A system is described for conjugating, isolating, and purifying proteins. The system contains an ultrafiltration apparatus which is connected with a reaction vessel reservoir.

9 Claims, 2 Drawing Sheets

SYSTEM FOR METHOD FOR THE MODIFICATION AND PURIFICATION OF PROTEINS

FIELD OF THE INVENTION

The invention relates to a continuous closed system for the multi-step reaction, modification, production, and purification of proteins as well as synthetic analogs thereof.

BACKGROUND OF THE INVENTION

A major task in chemical and biochemical syntheses concerns the purification of the desired reaction products from unwanted materials, including reagents, contaminants, by-products, solvents, etc. In a complex, multi-step synthesis, it is often necessary to conduct purifications at each of several critical steps in the synthetic process. Thus, separate isolation and purification procedures are usually employed for the reactant components, the intermediate and the final products of the synthesis with corresponding significant losses of material.

Such purifications must often be performed using specialized equipment and processes, which necessitates the transfer of reaction mixtures between reactant vessels and purification equipment. This is disadvantageous, because the methodology is inefficient and thereby complicates and prolongs manufacture. Moreover, the separate multi-step processes expose the product to the possibility of microbial and chemical contamination as well as the risk of degradation of the reagent or product at the various stages of synthesis thereby necessitating the inclusion of additional stringent process controls. This requirement for stringent process controls is particularly critical for the synthesis of pharmaceuticals.

As a consequence of the drawbacks of the prior art systems, there has been a pressing need for equipment which allows for the combination of the reaction and purification steps to the greatest degree possible. For example, peptide synthesis by solid phase methodology enables the intermediate purification steps to be conducted in the reaction vessel itself thereby reducing the presence of contaminant by-products. However, the complete purification of the cleaved peptide product may require several separate purification steps which result in loss of final product yield. (Stewart, et al. 1984 Solid Phase Peptide Synthesis; 2nd ed. Pierce Chemical Co., Rockford, Ill.)

The present invention provides a novel method that enables a general approach to liquid phase synthesis and product purification that is carried out in a single closed system.

SUMMARY OF THE INVENTION

The present invention is directed to a closed system for the continuous modification or conjugation of a protein and purification of the modified or conjugated protein product in a liquid phase. The system includes ultrafiltration apparatus, a reaction vessel, means for allowing the flow of the reaction solution from the reaction vessel to the ultrafiltration apparatus including the reverse flow from the ultrafiltration means and the reaction vessel, and a flow controlling means for regulating the flow thereof.

More than one ultrafiltration means may be incorporated for separating and purifying proteins and other molecules on the basis of molecular size in incremental orders of magnitude.

The closed system may also include a backwash reservoir which is fluidly connected to the ultrafiltration device for backwashing retained non-permeable peptides or proteins. The means for allowing the flow of reaction solution can be interconnecting tubing and the flow controlling unit may be made up of a pump and at least one valve. The pump in this system is preferably a circular or peristaltic type pump. The reaction vessel may also serve as a buffer reservoir in addition to a desalting reservoir.

The ultrafiltration means can be in the form of an ultrafiltration apparatus equipped with a spiral diafiltration cartridge, having a semi-permeable membrane having for example a molecular weight cutoff of 3,000; 5,000; 10,000; 15,000; 30,000 dalton; or higher. The aqueous system of the invention may also include a chromatographic device for separation of proteins from impurities or by-products by substrate affinity or size exclusion which is fluidly interconnected with reaction vessel and ultrafiltration device.

In certain embodiments the system of the invention may be automated with the use of electronical control means or may be entirely automated through the use of computerized process controls.

The invention provides a method for purifying a protein or a reaction product (coupled or conjugated protein) in a liquid closed system which comprises the steps of passing a protein or reaction mixture for the modification thereof in a liquid over a semipermeable membrane having a certain molecular retention cutoff contained in an ultrafiltration apparatus. The membrane selectively retains the protein or reaction product thereof on the basis of size. The protein or reaction product thereof retained on the membrane is washed extensively thereby removing the impurities which are not retained. The protein or peptide is then redispersed by backwashing or backflushing the membrane with the washing liquid, and concentrating and collecting the peptide or protein which is dissolved or suspended in the washing liquid. The concentrating, washing and backwashing cycles may be repeated for as many times as necessary for effective purification.

DETAILED DESCRIPTION OF THE INVENTION

Figure 1:
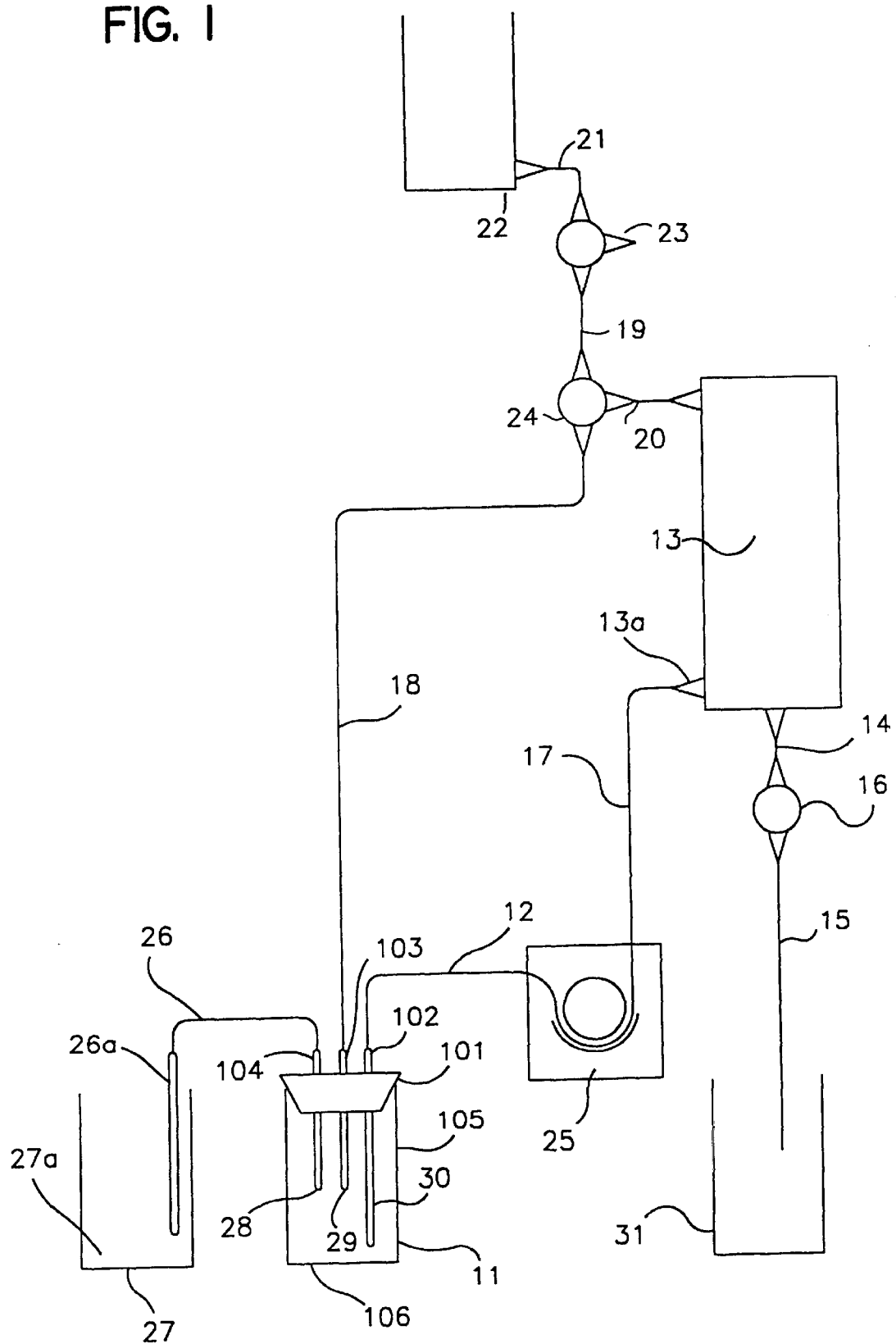
FIG. 1 illustrates a closed synthetic system apparatus utilizing an ultrafiltration device according to the invention.

By the definition adopted for this invention, peptide is understood as a molecule of up to 25 amino acids in length and proteins as a molecule of hundreds of amino acids, often cross-linked as a molecule cluster in various ways. The inventive system is envisioned, moreover, to afford derivatization or conjugation of a protein with each other, a peptide, a carbohydrate, or more specifically an immunotoxin, a radioactively labelled protein, and other moieties.

This invention provides a closed system combining the equipment for conducting a variety of chemical reactions with equipment for ultrafiltration purification. The selection of the specific reaction vessels in the system design depends on the chemical and physical constraints that are imposed by the type of reaction and its environment. It has been surprisingly found that a highly purified pharmaceutical product may be obtained with excellent yield by sequential or repetitive filtering and washing through different ultrafiltration type restraints, efficiently and effectively isolating the products through different suitable pore size filter membranes.

Ultrafiltration purification utilizes different semipermeable membranes to separate molecules based on size, shape and/or charge. Depending upon the chemical nature of the various constituents of a reaction system, an ultrafiltration membrane is selected that is permeable to removable constituents or reagents of the reaction system, but impermeable to those other constituents which are to be retained and concentrated above the membrane. The preferred filtration membranes should be inert with respect to the reactants as well as acid or salt components in the reaction solution. When the pressurized reaction mixture is passed over the ultrafiltration membrane, membrane-permeable constituents (permeate) pass through the membrane, thereby removing them from impermeable, retained constituents (retentate) of the mixture.

It has been found that the purification is particularly efficient if the ultrafiltration steps are alternated frequently by a backwashing step in order to diminish the presence and concentration of contaminants which may be entrapped in or on the filter, the retained protein or conjugate.

In accordance with a preferred embodiment of this invention, an apparatus containing a reaction vessel in fluid connection with at least one ultrafiltration device is used to conduct a reaction and purify the desired modified protein product(s). According to the methods of the invention, reaction steps are conducted in a liquid mixture or solution contained in the reaction vessel under appropriate temperature choice of liquid solvent or carrier and other control conditions. After the completion of the reaction, the reaction mixture is introduced into the ultrafiltration device for purification by pumping the mixture into the device or by some other means, such as e.g., gravity flow or vacuum. The purified reaction products can then be collected as a final product on the membrane, subsequently washed on the membrane or washed back into the reaction vessel for further reaction steps. Thus this recycling process feature of the invention is suitable for purifications to be performed at any stage of a synthetic pathway. This is especially useful in multi-stage syntheses which require purification of the intermediate products.

In a more preferred embodiment of the invention, the ultrafiltration utilizes a diafiltration unit which advantageously permits the reaction vessel to serve as a diafiltration buffer solution reservoir during the filtration and washing step. In addition, the method according to this invention readily provides a means for solvent/buffer exchange, concentration of reagent constituents and purification of the starting, intermediate and end products. The diafiltration can also be easily scaled up to very large volumes of production. In contrast, purification by traditional molecular sieve chromatography has very limited scale-up potential. The suitable diafiltration units for use in the invention are commercially available such as the diafiltration unit which contains a spiral diafiltration cartridge supplied by Amicon. Moreover, backwashing of the diafiltration unit helps in the extensive and successful purification/washing operation. Specifically, backwashing can be accomplished employing suitable washing solutions such as salt buffers.

If different ultrafiltration filters are required at separate stages in the synthetic process, an ultrafiltration apparatus can be used which allows for interchangeable filters so that filters can be changed depending on need, prior to each ultrafiltration step. Alternatively, different filter devices can be linked in series and furthermore interspaced with reaction vessels.

This invention is particularly adaptable for any protein synthesis where purification can be achieved by ultrafiltration and washing even though it is possible to add other component devices such as analytical or reverse phase HPLC or lyophilizing apparatus to the system. The preferred embodiment of this invention is very economical and efficient in that a single apparatus can be used to synthesize and purify the initial starting material, intermediate products and/or final products in a stepwise synthesis without intermittent removal or drying except for samplings. The closed liquid system of the invention can thus be used to synthesize or derivatize proteins and purify products under sterile conditions and thus results in a more environmentally safe procedure. In addition to the purification of reactants and products, the system provides economical means to concentrate the components and exchange solvents and buffers. The closed system which combines the reaction and purification steps can significantly reduce the time required for many synthetic processes, especially multi-step processes. Moreover, the closed system eliminates losses that normally occur with conventional unloading and loading transfer between different apparatuses.

A preferred embodiment of the invention provides a fully automated system which can be readily customized to suit specific requirements. The reaction vessel can be arranged to accommodate various volumes, temperatures, addition of inert gasses and color producing reagents, mixing, sampling, etc. The liquids may comprise aqueous or nonaqueous solvents. Aqueous solutions or buffers are used as appropriate. The ultrafiltration equipment can be selected to accommodate various volumes, temperatures, pressures and use different filters. The flexibility of the inventive system advantageously provides the opportunity to scale up from a small to a large scale production apparatus. Moreover, the combination is well suited for a wide variety of biochemical syntheses, including the synthesis or derivatization of protein based pharmaceuticals, and in particular products, such as e.g. hapten-immunogens, which require the chemical conjugation of one chemical moiety or peptide to a protein component, or antibodies coupled to another functional peptide, protein or nonprotein reagent. The component parts of the system are all commercially available and can include a wide variety of reaction vessels and ultrafiltration equipment.

A specific embodiment of the present invention provides a combination of a reaction vessel e.g., an open or covered beaker or flask connected to a reflux condenser which in turn is connected by pump and transfer line or tubing to a diafiltration device. A further modification of the present invention expands the closed system by interconnecting an affinity and/or a gel filtration column for a specific selection of the correct protein or derivative or conjugate thereof. The type of additional chromatographic devices which are connected to the closed system depends on the particular application. The closed liquid system according to the invention may also be linked to a solid state peptide synthesis system where the products may be eluted to the ultra- or diafiltration apparatus for purification and other subsequent treatment as may be appropriate.

The closed liquid system according to this invention may easily be controlled by computer connected to a series of electronic sensors and valve assemblies in order to automate the conjugated peptide purification, concentration and isolation in liquid form. For example, manual three-way valves may be replaced by corresponding solenoid valve units. In addition, pump speed rheostat controls may be replaced and regulated by flow and pressure sensors in appropriate placements within the fluid pathways connecting the reaction vessel and the ultrafiltration device on either side of the pump and the various valve assemblies. Similarly, automated controls or regulating units are in the fluid pathways connecting the optional reservoir and the ultrafiltration device. An automatic readout for an electronic sensing device for pH and ionic strength of the liquid within the diafiltration cartridge may also be provided.

The following examples are for illustration purposes only, and are not to be construed as limiting this invention.

EXAMPLE 1

The apparatus 10 of this example is depicted schematically in FIG. 1. The apparatus 10 is fluidly connected between the reaction vessel 11 and the ultrafiltration/diafiltration device 13 through a suitable fluid pathway such as tubing 12 provided with flow control means such as a valve or pump at 25. The liquid phase of the reaction solution containing reagents and products can be moved from the reaction vessel 11 through a suitable peristaltic pump 25 into the filtration unit 13. The Diafiltration Reservoir 27 is connected through the reaction vessel 11 to the filtration unit 13 for washing/rinsing of the retentate which is accumulated on the membrane of the filtration unit. The permeate or filtrate can be drained from the filtration unit 13 into the reservoir 31. The Backflush Reservoir 22 supplies a solution for removing the retentate in a counterflow direction through the ultrafiltration unit 13 into the reaction vessel 11 or other suitable receptacle. Optionally, the fractionation of the protein or peptide containing the reaction products may be sequentially separated into size-graded fractions by using filters with a molecular weight cutoff with an order of magnitude difference in molecular weight or as required to separate the products.

Figure 2:
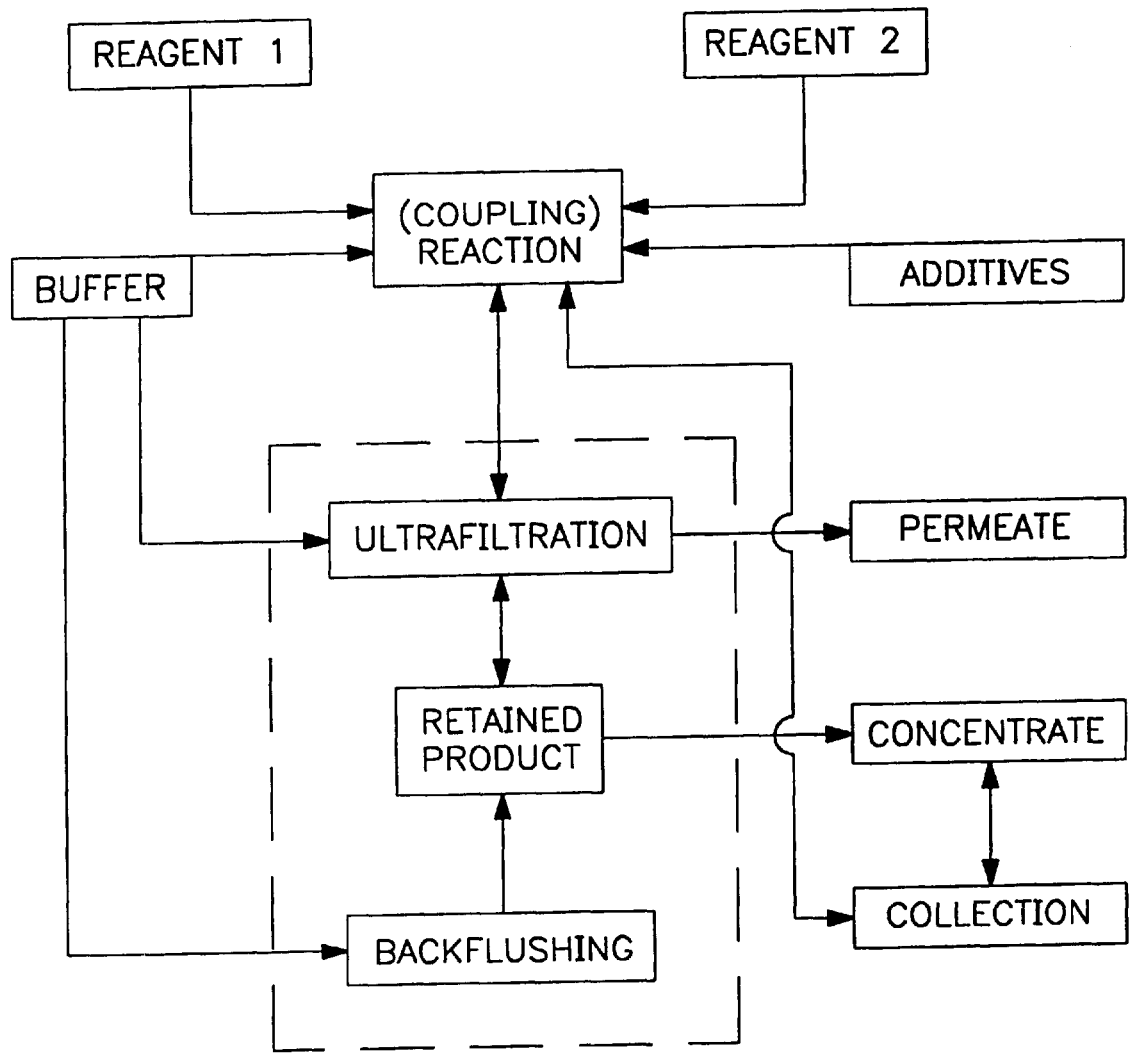
FIG. 2 is a flow chart showing the sequential operations utilizing the closed liquid system apparatus in an embodiment of the invention of FIG. 1.

The principle operational steps for the system depicted in FIG. 1 shown are outlined in the flow chart shown in FIG. 2. It is clear, however, that several combinations of steps and embodiments can be envisioned involving a first purification of least one of the reagents involved in a subsequent modification reaction such as conjugation/coupling with one or more other reagents such as proteins, peptides or non-protein molecules such as carbohydrates.

According to the embodiment illustrated in FIG. 2, the reaction mixture containing a protein (Reagent 1), modifying or conjugating reagents (Reagent 2) and other components (Additives), is fluidly transferred to the ultrafiltration apparatus, washed with a washing buffer solution (Buffer), removing the solution containing filter membrane permeable material (Permeate) and retaining and concentrating the filter membrane impermeable material. The retained product can be repeatedly redispersed from the membrane by backflushing, and again washed, reconcentrated, and finally removed from the ultrafiltration means and collected in the reaction vessel for analysis or further modification.

Specific part numbers and manufacturers are listed for the various components of the apparatus; however, it is recognized that comparable equipment from other commercial sources may be substituted without diminishing the effectiveness of the apparatus, and it should also be understood that the apparatus can be scaled up to any required level of production without departing from the principles of the invention.

Referring to the embodiment illustrated in FIG. 1, the system may be described in more detail, as follows. The reaction vessel 11 is a 2000 ml, type 1 glass, amber, wide mouth bottle (Wheaton). This vessel was selected based on the following criteria: (i) the 2000 ml capacity accommodates reaction volumes from 100 ml to 1800 ml; (ii) type 1 glass conforms to USP standards for pharmaceutical manufacture; (iii) amber color glass 106 of the vessel 11 limits the penetration of light capable of degrading the light-sensitive chemical crosslinking agent used in the synthesis; and (iv) the wide mouth provides clearance for a stopper 101 fitted with 3 tubes, and it allows easy access for reagent additions and sampling. The wall 105 of the reaction vessel 11 is marked for volume of solution in the vessel, in 100 ml increments. The reaction vessel 11 is capped with a neoprene stopper, which is bored with 3 holes 102, 103, 104, which are equally spaced and located diagonally across the stopper.

Type 1 borosilicate glass tubing of suitable I.D., is passed through each of the 3 holes in the stopper. The reaction vessel is provided with suitable tubing 30, connected with the pump, and positioned within the vessel so as to effectively evacuate the vessels contents when the pump is in operation. The Tubing 30 is also positioned towards the wall of the reaction vessel to provide clearance for a mixing device such as a stirring bar. The Tubings 28 and 29 are connected with plastic tubing (preferably Pharmed) to Valve 24 and to the Diafiltration Solution Reservoir 27, respectively.

Pharmed tubing, ¼ inch I.D. with ¹⁄₁₆ inch wall (#AYX42017, Norton), connects the various fluid ports of the apparatus, with the exception of the tubing 12 that runs through the pump 25, which is ⅝ inch I.D. with ¹⁄₁₆ inch wall (#AYX42022, Norton). This tubing was selected because it is opaque to light (and thereby protects light-sensitive reagents), can be sterilized by autoclaving, is compatible with the peristaltic pump and can withstand the perssures of the ultrafiltration unit. Tubing connections (not shown in detail) are secured with snapper clamps, 8.9–10 mm diameter (#C6096-2, Baxter Scientific Products).

The exact length of tubing sections is not critical to the operation of the apparatus; however, it is desirable to keep tube lengths as short as practicable to minimize intratube volume. The connective tubings in the apparatus 10 of FIG. 1 are as follows: Tubing 12 from Reaction Vessel Glass Tubing 30 to Ultrafiltration Unit 13 (through pump); Tubing segment 20 from Ultrafiltration Unit 13 to Valve 24; Tubing segment 18 from Valve 24 to Reaction Vessel Glass Tubing 29; Diafiltration Solution Reservoir Glass Tubing 26 to a Reaction Vessel Glass Tubing 28; Tubing 14 from Ultrafiltration Unit 13 to Valve 16; Tubing 15 from Valve 16 to Permeate Reservoir 31; Tubing 20 from Ultrafiltration Unit 13 to Valve 24.

The valves 23, 24, 16 are made of polypropylene and Teflon. Valve 23 is a built-in part of the separatory funnel that comprises the Backwash Reservoir. Valve 24 is a 3-way stopcock (#64700004, Nalgene) and Valve 16 is a 2-way stopcock (#64600004, Nalgene).

The peristaltic pump 25 is a Model LP1 (Amicon). It is the variable speed, type which allows for adjustment of filter input pressure, and it is reversible. The pump's delivery rate and pressure are matched to the capacity of the Ultrafiltration Unit 13.

The Ultrafiltration Unit 13 consists of a spiral membrane cartridge diafiltration concentrator (#54118, Amicon) fitted with a spiral wound membrane cartridge having a suitable molecular weight cut-off. The diafiltration concentrator was selected because its capacity is compatible with the usual reaction volume of the small volume capacity of this embodiment.

The Backwash Reservoir 22 consists of a 500 ml glass separatory ("Buchner") funnel (#6402, Pyrex) that contains an integral 2-way stopcock valve (Valve 23 in FIG. 1).

The Diafiltration Reservoir 27 consists of a 2 L glass Pyrex media bottle (13952-L, Corning). The diafiltrate solution take-up tube 26a consists of type 1 borosilicate glass tubing, and is attached to the connective tubing 26 (leading to the Reaction Vessel 11) and extends into the Diafiltration Reservoir 27.

The Permeate Reservoir 31 consists of a 2 L glass Pyrex media bottle (13952-L, Corning).

Operation 1: Reaction.

Reactions such as for example the chemical conjugation of a short peptide to a larger protein are conducted in the Reaction Vessel 11 while Valves 23, 24 and 16 are closed and the Pump 25 is not operated. The diafiltration pickup tube 26a is not immersed into the Diafiltration Solution Reservoir 27. Reactants are added to the vessel via opening 101. (Tubing for reagent addition and sample removal tubing can be added to the Reaction Vessel setup, if necessary.) Opening 101 is closed during the reaction period. The reaction mixture is stirred, and the reaction is allowed to proceed to completion. Samples can be withdrawn from the Reaction Vessel to monitor the progress of the reaction.

Operation 2: Purification.

Purifications are conducted by diafiltration. Valve 23 is closed. Valve 24 is opened to allow filtered sample to flow from the Ultrafiltration Unit to the Reaction Vessel. Valve 16 is opened to allow permeate (waste material that passes through the filter) to pass into the Permeate Reservoir 31. The Diafiltration Solution Reservoir 27 is filled with diafiltration solution and the glass tubing 26a for diafiltration solution pickup is inserted reaching to the bottom 27a of the Diafiltration Solution Reservoir. The material to be purified is added to the Reaction Vessel 11, which is then closed. The Pump 25 is used to transfer solution from the Reaction Vessel 11 through the inlet port 13a into the Ultrafiltration Unit 13. The Ultrafiltration Unit 13 is operated under the recommended inflow and backpressures by adjusting Pump speed and the Ultrafiltration Unit's 13 integral backpressure valve per the manufacturer's recommendations.

The progress of purification is monitored by testing samples obtained from the tubing leading to the Permeate Reservoir 31 which receives the filtrate drainage of the reaction solution as well as the washing solution. The Diafiltration Solution Reservoir 27 is refilled when low on solution; the Permeate Reservoir 31 is emptied or replaced when appropriate.

When permeate testing indicates that purification is complete the diafiltration solution intake is terminated by for example raising Tubing 26a out of the diafiltrate solution in Diafiltration Solution supply vessel 27, and the remaining solution is allowed to pass into the Reaction Vessel 11. Valves 24 and 16 are closed. The test solution in the Ultrafiltration Unit 13 and the tubing 17 can then be collected in the Reaction Vessel by draining or backflushing (see Operation 4).

The purification operation can also be used to exchange buffers. The same process is followed as for purification, except that the new solvent/buffer is added to the Diafiltration Solution Reservoir 27. The purification process is allowed to proceed until the old solvent/buffer has been replaced.

Operation 3: Concentration.

To concentrate solutions in the Reaction Vessel 11, the appropriate buffer or storage solution is added to the Reaction Vessel 11 and Valve 23 is closed and Valve 24 is opened to allow flow from the Ultrafiltration Unit 13 to the Reaction Vessel 11. Valve 16 is opened to allow permeate to flow from the Ultrafiltration Unit 13 to the Permeate Reservoir 31. The diafiltrate uptake tubing 26a is not placed into the Diafiltration Solution Reservoir 27 (to enable air to pass through the tube.) The Pump 25 and the Ultrafiltration Unit 13 are then operated as for the Purification Operation. During the concentration process, the level of solution in the Reaction Vessel 11 must be monitored to ensure that Tubing 30 remains immersed in the solution as the solution level drops. When concentration is complete, the pump 25 is switched off and all Valves 16, 23, 24 are closed. The solution (containing reaction product) in the Ultrafiltration Unit 13 and the tubing 17, 18 can then be drained or backflushed into the Reaction Vessel (see Operation 4).

Operation 4: Draining/Backflushing.

To recover solution containing the reaction product from the Ultrafiltration Unit 13 and the tubing 17, 18 at the conclusion of purification and concentration operations, it is necessary to drain this solution from these components into the Reaction Vessel 11. To perform this operation step, the diafiltration solution uptake tube 26a is not lowered into the Diafiltration Solution Reservoir 27, thereby allowing air to pass through the diafiltration tube. Valve 16 is closed. Valve 23 is opened to allow air to pass from the Backwash Reservoir (which is empty) through Valve 23 to Valve 24. Valve 24 is then opened to allow air to pass from Valve 23 to the Reaction Vessel 11, thus draining those tubings 18, 19. To drain the Ultrafiltration Unit 13, Valve 24 is then adjusted to allow air to pass from Valve 23 to the Ultrafiltration Unit 13. The Pump 25 is activated, in reverse mode, such that the solution with the reaction product flows from the Ultrafiltration Unit 13 through the Pump 25 into the Reaction Vessel 11. When drainage is complete, the Pump 25 is switched off and Valves 23 and 24 closed.

To backflush the Ultrafiltration Unit 13, the same procedure is followed as for drainage of the Ultrafiltration Unit 13, except that the desired volume of backwash solution is added to the Backwash Reservoir 22. Thus, when Valve 23 is opened, only the backwash solution, but not air will flow from the Backwash Reservoir 22 through the Valve 24 into the Ultrafiltration Unit 13 and finally into the Reaction Vessel 11 as receptacle. When backwashing is complete (e.g., the products have been removed), the Pump 25 is switched off and the Valves 23, 24 are closed.

EXAMPLE 2

This example concerns the synthesis of the conjugate peptide immunogen comprising peptide of amino acid sequence hG17 (1–9)Ser9 conjugated to Diphtheria toxoid (DT) protein carrier. The process of this example is designed for the synthesis of a peptide-protein conjugate that is used for the induction of antibody responses to human gastrin 17 ("hG17"). The equipment and techniques used to synthesize this conjugate by traditional procedures are described in U.S. Pat. No. 5,023,077, Example 1, which specification is incorporated herein by reference.

Step 1: DT Purification.

The DT is provided in a solution that contains other low molecular weight constituents, including 0.3 M glycine and 0.01% thimerosal. These other constituents have to be removed before the conjugation process can begin. The DT is purified by a series of diafiltration and concentration steps using the ultrafiltration unit 13. Each diafiltration uses a volume of deionized water a diafiltrate solution equal to 5 times the sample volume present in the reaction vessel 11. To prevent filter clogging, backwash procedures using backflushing from the reservoir 22 are also incorporated into the diafiltration process. Once the diafiltration procedure for DT purification is completed, phosphate buffer (0.5 M sodium phosphate) is substituted using three cycles of diafiltration with 5 fold volumes to prepare for DT activation reaction with EMCS (Epsilon—maleimidocaproic acid N-hydroxysuccinimide ester). At the conclusion of Step 1, the solution is concentrated to about 20–25 mg DT/ml in the ultrafiltration unit 13 (equipped with a spiral wound membrane cartridge of 30,000 MW cut-off; Amicon, YM30S1) by judicious removal of permeate washing solution and by backflushing pure DT into the reaction vessel 11. DT purity is analyzed by HPLC and the concentration of DT is determined.

Step 2: Activation of the Purified DT with EMCS.

The purified DT is next activated with EMCS, to yield maleimido-DT (MDT). In this step, the succinimidyl moiety of EMCS reacts with free c-amino groups on DT, coupling the EMCS to DT such that the EMCS maleimido group is left to bind peptide (in Step 4).

Of the approximately forty amino groups present per $10^5$ molecular weight of DT protein, about twenty-five are activated in the present synthesis. To achieve this level of activation, a 4-fold molar excess of EMCS to DT amino groups is required. The concentration of DT to be activated is adjusted to 20 mg/ml (±5 mg/ml) and added back to the reaction vessel. The EMCS is added and maleimido DT (MDT) is formed over a 2 hour reaction period.

Step 3: Purification of MDT.

Non-reacted and hydrolyzed EMCS are next removed from the MDT solution by transferring the reaction mixture from the reaction vessel 11 a series of diafiltration, backwash and concentration steps (as described above) which involve cycling a citrate washing solution from the reaction vessel 11 through the ultrafiltration device 13, removing the filtrate to reservoir 31, alternately backwashing from reservoir 22 and concentrating the retained MDT in device 13, and finally restore the purified MDT to the reaction vessel 11. In the course of these procedures, citrate (0.1 M sodium citrate) coupling buffer is completely substituted for the phosphate buffer. At the conclusion of this step, the quantity of MDT and its degree of activation are determined.

Step 4: Conjugation of hG17 (1–9)Ser9 Peptide to MDT.

The 500 mg of hG17 (1–9)Ser9 peptide is dissolved in 25 ml of nitrogen gas saturated 0.1 M sodium citrate (SC) and coupled to the activated MDT by gradually adding the purified peptide solution to the purified MDT solution containing 1.17 g MDT at 20 mg/ml 0.1 MSC in the reaction vessel 11 and allowing the coupling reaction to proceed for a suitable time period to completion. Peptide is added at a 1.1:1 molar ratio of peptide:maleimido group (in MDT) to achieve the desired substitution ratio of 25 moles peptide Step 5: Conjugate Purification and Lyophilization.

The conjugate reaction solution (83.5 ml) was diluted to 1.0 L-volume with 0.2 M ammonium bicarbonate solution (AB) followed by about 5 fold concentration to a volume of approximately 100 mls. This was followed by closed system diafiltration of the solution over a spiral wound membrane of 30,000 dalton cut-off in the ultrafiltration unit 13 with 500 ml of AB solution effectively retaining only the conjugate and a backwash with 100 ml of AB solution then concentration of the product solution back to 100 ml. This diafiltration-backwash-concentrate process was repeated two more times, followed by 3 cycles of diafiltration-backwash-concentrate process in distilled water. After this final treatment, the system tubing and the membrane cartridge were drained to remove traces of AB. The conjugate solution itself was removed from the reaction vessel and diluted to approximately 2 mg/ml in $H_2O$ and then lyophilized to remove or sublimate any residual AB. The yield of conjugate was found to be 1.4 gm.

The conjugate was analyzed by HPLC and found to contain a single peak indicating homogeneity. By contrast, conjugate produced by the previous methodology was shown by HPLC analysis not to be pure as it contained about three distinct peaks. In addition, the synthesis in this example took only 1½ days to complete, which is far superior to the 3 days required to perform the synthesis by the previous methodology.

What is claimed is:

1. A method for conjugating a protein to another molecule and purifying the conjugated produce thereof in a closed liquid system, essentially consisting of the steps of:

(a) conjugating of a protein molecule to another molecule in a liquid reaction mixture, so as to form a mixture of conjugated and unconjugated protein and other molecules;

(b) ultrafiltering the liquid reaction mixture containing conjugated and unconjugated protein and other molecules so as to isolate the retentate of conjugated protein molecules on the ultrafilter of an ultrafiltration means;

(c) washing the isolated retentate of conjugated protein molecules on the ultrafilter with a desalting solution, water or another buffer solution;

(d) backwashing the ultrafiltration means with a buffer solution from a backwash reservoir to release and disperse the retentate of conjugated protein molecules from the ultrafiltration means;

(e) purifying the conjugated protein molecules by repeating the steps (c) and (d) until the conjugated protein molecules are substantially free of the non-conjugated molecules; and (f) recovering the retentate of conjugated protein molecules from the ultrafiltration means, or retransferring the retentate to the reaction vessel from the ultrafiltration means for further modification.

2. A method for purifying a protein reagent in a liquid mixture in a closed system which essentially consists of the steps of passing the liquid mixture over a semipermeable membrane of sufficiently small pore size contained in an ultrafiltration apparatus, so as to selectively retain the protein on the membrane; washing the retained protein on the membrane; backwashing the protein from the membrane with washing liquid from a backwash reservoir, and harvesting the washing liquid containing the retained protein.

3. The method for purifying a protein according to claim 2, wherein the protein is activated, conjugated, or modified in the liquid mixture before being passed over the semipermeable membrane.

4. The method for purifying a protein according to claim 2, wherein the steps of washing and backwashing are repeated at least once.

5. The method of purifying a protein according to claim 2, wherein the ultrafiltration apparatus contains a diafiltration means.

6. The method of purifying a protein according to claim 2, wherein the semipermeable membrane has a molecular weight cutoff selected from the group of 5,000, 15,000 and 30,000 and 100,000 dalton.

7. The method of purifying a protein according to a claim 2, further comprising sterile conditions.

8. The method of claim 3, wherein the immunogenic conjugate comprises a purified preparation of a sterile human vaccine.

9. The method of claim 1, wherein the conjugated product is an immunogen comprising an immunomimic peptide and an immunogenic carrier protein.

* * * * *